United States Patent [19]

Machida et al.

[11] 4,386,076
[45] May 31, 1983

[54] (E)-5-(2-HALOGENOVINYL)-ARABINOFURANOSYLURACIL, PROCESS FOR PREPARATION THEREOF, AND USES THEREOF

[75] Inventors: Haruhiko Machida; Shinji Sakata, both of Choshi, Japan

[73] Assignee: Yamasa Shoyu Kabushiki Kaisha, Chiba, Japan

[21] Appl. No.: 215,928

[22] Filed: Dec. 12, 1980

[30] Foreign Application Priority Data

Dec. 19, 1979 [JP] Japan .............................. 54-164025

[51] Int. Cl.³ ...................... A61K 31/70; C07H 19/06
[52] U.S. Cl. ........................................ 424/180; 536/23
[58] Field of Search ........................... 536/23; 424/180

[56] References Cited

U.S. PATENT DOCUMENTS 4,247,544  1/1981  Bergstrom et al. ................... 536/23

OTHER PUBLICATIONS

Machida, H. et al., Antimicrobial Agents and Chemotherapy, vol. 17, pp. 1030–1031, 1980.
Cheny, Y. et al., Antimicrobial Agents and Chemotherapy, vol. 18, pp. 957–961, 1980.
Sakata, S. et al., Nucleic Acids Research, Symposium Series No. 8; 539–542, 1980.
Machida, H. et al., Antimicrobial Agents and Chemotherapy, vol. 20, pp. 47–52, 1981.
Honjo, M. et al., Chem. Pharm. Bull., vol. 15, pp. 1076–1079, 1967.
Lipkin and Rabi, J. Am. Chem. Soc., vol. 93, pp. 3309–3310, 1971.
Renis, H., Cancer Research, vol. 30, pp. 189–194, 1970.
Bärwolff, D. and Langen, P., Nucleic Acids Research, Special Publication No. 1, 529–531.
Bleackley, R. et al., Tetrahedron, vol. 32, pp. 2795–2797, 1976.
De Clercq, E. et al., Proc. Natl. Acad. Sci., vol. 76, pp. 2947–2951, 1979.

*Primary Examiner*—Blondel Hazel
*Attorney, Agent, or Firm*—Wenderoth, Lind & Ponack

[57] ABSTRACT

A novel compound, (E)-5-(2-halogenovinyl)-arabinofuranosyluracil; a process for producing the same comprising reacting 5-vinylarabinofuranosyluracil with a halogen; and use of the same as an anti-DNA virus agent, especially anti-herpes virus agent and anti-varicella-zoster virus agent.

6 Claims, No Drawings

(E)-5-(2-HALOGENOVINYL)-ARABINOFURANOSYLURACIL, PROCESS FOR PREPARATION THEREOF, AND USES THEREOF

BACKGROUND OF THE INVENTION

1. Field of the Invention

This invention relates to a novel compound, (E)-5-(2-halogenovinyl)-arabinofuranosyluracil (hereinafter referred to as 5-halogenovinyl-araU), a process for preparation thereof, and uses thereof.

The present compound 5-halogenovinyl-araU is a compound represented by the formula [I],

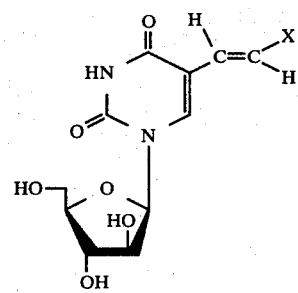

wherein X stands for a halogen such as bromine, chlorine, or iodine. The compound [I] is useful as a medical drug such as an anti-virus agent since it has a strong anti-virus activity and has only a slight inhibitory activity on cell proliferation.

2. Description of the Prior Art

The following compound [II], 5-vinylarabinofuranosyluracil (hereinafter referred to as 5-vinyl-araU), which can be considered to be a precursor of the compound [I] with respect to the halogenation thereof, has been known together with its process for preparation as well as its physiological activity, that is, a strong inhibitory action on the infection and proliferation of herpes virus with almost no inhibiting action on proliferation of normal cells (cf. K. Ikeda et al.: Abstracts of Papers, the 99th Annual Meeting of Pharmaceutical Society of Japan, Page 213, 30C 10-2).

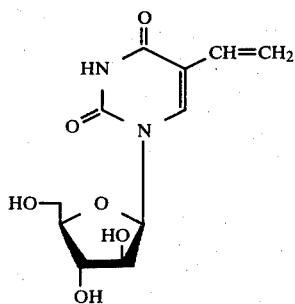

The 2'-deoxyribose derivatives of 5-vinyluracil and halo derivatives thereof are also known together with the process for their preparation, and the physiological activity thereof. Reference is made to E. De Clercq et al.: Proc. Natl. Acad. Sci. USA, Vol. 76, No. 6, PP. 2947-2951, June 1979, Medical Sciences.

These disclosures of the prior art, however, make no mention of 2-halo derivatives of the compound having the formula [II], their physiological activities, and how to prepare them.

SUMMARY OF THE INVENTION

According to this invention in one aspect thereof, there are provided 2-halo derivatives of the above-mentioned compound [II], which are believed to be novel compounds.

Each of these 2-halo derivative compounds is an (E)-5-(2-halogenovinyl)-arabinofuranosyluracil represented by the formula [I],

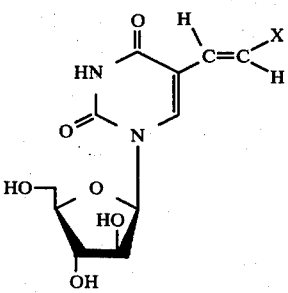

wherein X stands for a halogen.

The typical compounds thereof are those wherein the halogen (X) is chlorine, bromine, and iodine.

According to the present invention in another aspect thereof, there is provided a process for preparation of the compounds of the formula [I], which is characterized by reaction of the compound of the following formula [II] with a halogen.

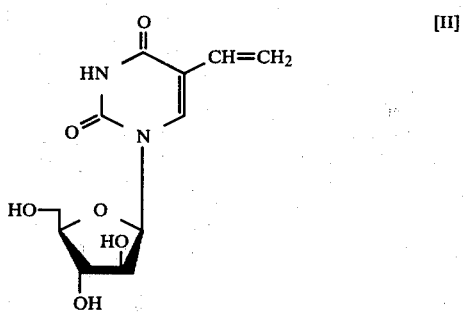

This reaction is conveniently carried out in a common solvent for both 5-vinyl-araU of the formula [II] and the halogen used.

In accordance with the present invention in still another aspect thereof, there is also provided an anti-DNA virus agent comprising an effective quantity of a compound of the formula [I]. The anti-DNA virus agent generally comprises a compound of the formula [I] and a pharmaceutically acceptable carrier. A typical example of the agent is an anti-herpes virus agent.

As is clear from the experimental data given hereinafter, the compound [I] of the present invention has a greater anti-virus activity than the compound [II], which may be said to be a parent compound of the compound [I], and less inhibitory action on cell proliferation than the 2'-deoxyribose derivatives thereof. Such characteristic physiological activity of the compound [I] could not have been anticipated by those skilled in the art. Moreover, while the compound [I] of the present invention is prepared by reaction of the compound [II] with a halogen, no one would have expected that the compound could be obtained by such a simple reaction.

While it may be presumed that this reaction, in its reaction mechanism, comprises the addition of the halogen and the removal of the hydrogen halide from the intermediate addition product, there has been no report on such a reaction of addition of a halogen to a 5-vinyl group and removal of hydrogen halide at the nucleoside level.

DETAILED DESCRIPTION OF THE INVENTION

Compound [I]

The compound of the present invention is a 5-halogenovinyl-araU represented by the formula [I]. Typical examples thereof are those wherein the halogen (X) is chlorine, bromine, or iodine, especially those wherein X is chlorine or bromine.

Physical and chemical properties of the typical compounds according to the present invention are shown in Examples 1 and 2 set forth hereinafter.

Synthesis of the Compound [I]

The 5-halogenovinyl-araU of the formula [I] can be prepared by any process which is appropriate with respect to the formation of the desired bonds and introduction of desired atomic groups.

One such suitable process comprises the reaction of 5-vinyl-araU of the formula [II] with a halogen.

This reaction is preferably carried out in a solution of the 5-vinyl-araU and the halogen used. Suitable solvents are anhydrous polar solvents such as dimethylformamide, dimethylacetamide, the dimethylsulfoxide. The reaction is preferably carried out using 1 to 1.1 equivalent of halogen per 1 equivalent of 5-vinyl-araU. The reaction is generally performed at room temperature to 100° C. for 1 to 4 hours. As stated hereinabove, the halogenation reaction may comprise the step of addition of a halogen to the vinyl group and the step of removal of a hydrogen halide from the addition product, but the reaction may be regarded as a single-step reaction thanks to the high velocity of the addition of halogen.

The isolation of the resulting 5-halogenovinyl-araU from the reaction mixture and the purification thereof can be carried out by conventional methods. For example, conventional purification steps can be suitably selected and combined, examples of such steps being adsorption chromatography in which silica gel or an adsorptive resin is used as a carrier, ion-exchange column chromatography, and recrystallization.

Some specific examples of synthesis are shown in Examples 1 and 2. However, modifications of these examples and selection of the optimum conditions for given reactants will be obvious to those skilled in the art.

The 5-vinyl-araU to be halogenated is known in the art, and can be readily prepared if necessary according to the above-mentioned prior art.

Anti-DNA Virus Agent

The 5-halogenovinyl-araU of the formula [I] has a low inhibitory action on cell proliferation in spite of its high anti-virus activity and therefore can be used advantageously as an effective component of anti-DNA virus agents.

The anti-DNA virus agent in accordance with the present invention comprises 5-halogenovinyl-araU of the formula [I] and preferably further comprises a pharmaceutically acceptable carrier.

5-halogenovinyl-araU can be used for the prevention and treatment of diseases such as DNA virus infections, specifically, various herpetic diseases (such as keratitis, skin infections, genital infections, and encephalitis) and varicella-zoster infections. The anti-DNA virus agent used for this purpose should contain an effective quantity of the compound [I].

The mode of administration and dosage form of the anti-DNA virus agent comprising the compound [I] depend upon the given DNA virus-disease. More specifically, a suitable and typical dosage form is, for example, an ointment in the case of percutaneous administration and an eye lotion in the case of administration onto the conjunctiva.

The doses of the anti-DNA virus agent should be determined by physicians in accordance with the conditions of given DNA virus-diseases. More specifically, the suitable dose of compound [I] may be, for example, within the following ranges.

Intravenous injection: 0.1 to 5 g/body
Oral administration: 0.1 to 5 g/body

Eye-drop agents and ointments may contain 0.01 to 1% and 0.01 to 10%, respectively, of the compound [I].

One of the marked characteristics of the compound [I] is its low toxicity or low inhibitory action on cell proliferation. The acute toxicity of the compound [I] is such that the $LD_{50}$ of the compound [I] administered either intraperitoneally, orally or subcutaneously is estimated to be more than 10,000 mg per kg. The value administered intravenously is estimated to be more than 200 mg/kg.

The compound [I] generally exhibits a high anti-virus activity. The degree of the anti-virus activity thereof, however, depends to some extent on the type of DNA viruses to be treated. For example, to the best of our knowledge, the anti-virus activity of the compound [I] wherein X is bromine on type-2 herpes (HSV-2) is lower than that on type-1 herpes (HSV-1). In the anti-HSV-2 activity, the compound, as well as the corresponding 2'-deoxy derivative, is inferior to 5-vinyl-araU.

As mentioned above, the typical DNA viruses for which the present invention is intended are herpes virus and varicella-zoster virus. The compound [I], however, can be expected to exhibit ample anti-virus activity against the other DNA viruses such as, for example, DNA viruses which induce deoxypyrimidine nucleoside kinase peculiar to the viruses after infection, since the compound [I] may be phosphorylated only by the deoxypyrimidine nucleoside kinase and the triphosphate derivative thus formed may be capable of being an inhibitor to DNA-polymerase.

In order to indicate more fully the nature and utility of this invention, the following specific examples of practice are set forth, it being understood that these examples are presented as illustrative only and that they are not intended to limit the scope of the invention.

EXAMPLE 1

In 15 ml of dried dimethylformamide was dissolved 260.2 mg of 5-vinyl-araU. To the solution was then added a bromine solution which had been prepared by dissolving 79.9 mg of freshly distilled bromine in 3 ml of dried dimethylformamide. The mixture was subjected to reaction at 100° C. for 1 hour. The reaction product was then cooled and concentrated under reduced pressure at a temperature not higher than 30° C. The resulting residue was washed with benzene and then with ethyl ether and was dissolved in a small quantity of methanol. The resulting solution was charged onto 10 preparative thin-layer chromatoplates (PTLC), each being 20 cm×20 cm carrying 10 g silica gel on it, and developed 3 times with chloroform-methanol (6:1). The part containing the desired product was scraped off from the plates and subjected to extraction with 270 ml of chloroform-methanol (8:1). Silica gel was removed by filtration, and the filtrate was concentrated to dryness under reduced pressure, whereupon 159 mg of a powder (yield 47.3%) of (E)-5-(2-bromovinyl)-1-$\beta$-D-arabinofuranosyluracil (hereinafter referred to as 5-bromovinyl-araU) was obtained. A part of the resulting powder was recrystallized from ethanol to obtain white crystalline powder of the following properties.

Melting Point 195° to 200° C. (decomposed) Elemental Analysis (as $C_{11}H_{13}N_2O_6Br$) Calculated (%) C: 37.84 H: 3.75 N: 8.02 Found (%) C: 37.77 H: 3.62 N: 8.13

Ultraviolet Absorption Spectrum
$\lambda_{max}^{H2O}$ 250, 293 nm $\lambda_{min}^{H2O}$ 272 nm
$\lambda_{max}^{0.05N-HCl}$ 251, 292 nm $\lambda_{min}^{0.05N-HCl}$ 272 nm
$\lambda_{max}^{0.05N-NaOH}$ 257, 284 (sh) nm $\lambda_{min}^{0.05N-NaOH}$ 237 nm Nuclear Magnetic Resonance (NMR) Spectrum ($\delta$, ppm, DMSO-$d_6$)

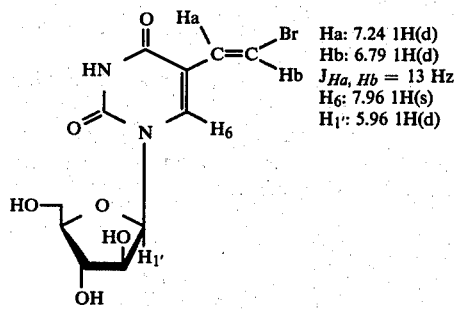

Ha: 7.24 1H(d)
Hb: 6.79 1H(d)
$J_{Ha, Hb}$ = 13 Hz
H$_6$: 7.96 1H(s)
H$_{1'}$: 5.96 1H(d)

3 times with chloroform-methanol (6:1). The part containing the desired product was scraped off from the plates and extracted with 300 ml of chloroform-methanol (5:1). Silica gel was removed by filtration and the filtrate was concentrated to dryness under reduced pressure, whereupon 135 mg of a powder (yield 39.9%) of (E)-5-(2-chlorovinyl)-1-$\beta$-D-arabinofuranosyluracil (hereinafter referred to as 5-chlorovinyl-araU) was obtained. A part of the resulting powder was recrystalized from methanol to obtain 47 mg of white needle crystals of the following properties.

Melting Point 221.5° C. Elemental Analysis as $C_{11}H_{13}N_2O_6Cl$ Calculated (%) C: 43.36 H: 4.30 N: 9.19 Found (%) C: 43.08 H: 4.12 N: 8.93

Ultraviolet Absorption Spectrum
$\lambda_{max}^{0.1N-HCl}$ 247, 292 nm
$\lambda_{max}^{0.1N-NaOH}$ 254, 286 (sh) nm NMR Spectrum ($\delta$, ppm, DMSO-$d_6$)

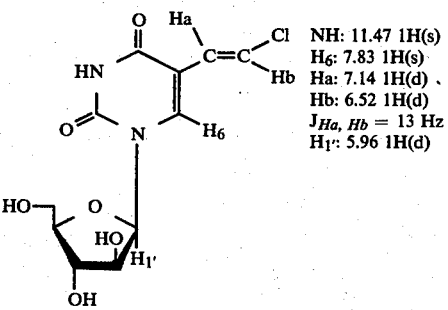

NH: 11.47 1H(s)
H$_6$: 7.83 1H(s)
Ha: 7.14 1H(d)
Hb: 6.52 1H(d)
$J_{Ha, Hb}$ = 13 Hz
H$_{1'}$: 5.96 1H(d)

Pharmacological Test 1

In accordance with the Sidwell et al. method (cf. Applied Microbiology, Vol. 22, No. 5, P. 797, 1971), the anti-virus activities of 5-bromovinyl- and 5-chlorovinyl-araU on human embryonic lung fibroblasts (HEL-F) were determined by using as controls 5-iodo-2'-deoxyuridine (IDU) and arabinofuranosyladenine (araA). The results are shown in the following table.

| | Compounds tested | | | | | | | |
|---|---|---|---|---|---|---|---|---|
| | 5-bromo-vinyl araU | | 5-chloro-vinyl araU | | IDU | | araA | |
| | Anti-virus activity | | | | | | | |
| Viruses | MIC* ($\mu$g/ml) | VR** | MIC* ($\mu$g/ml) | VR** | MIC* ($\mu$g/ml) | VR** | MIC* ($\mu$g/ml) | VR** |
| HSV-1, VR-3[1] | 0.032 | 3.8 | 0.1 | 3.3 | 3.2 | 2.4 | 10 | 1.9 |
| HSV, isolate-1[2] | 0.032 | 3.8 | 0.1 | 3.1 | 3.2 | 2.1 | 10 | 1.9 |
| VZV[3] | 0.1 | 3.5 | 0.1 | 3.4 | 3.2 | 2.3 | — | — |

(note)
*MIC = minimal inhibitory concentration for cytopathogenic effect caused by the infection
**VR = virus rating
[1]HSV-1, VR-3 = herpes simplex virus type 1 VR-3 strain
[2]HSV, isolate-1 = herpes simplex virus clinical isolated strain - 1
[3]VZV = varicella-zoster virus

EXAMPLE 2

In 15 ml of dried dimethylformamide was dissolved 300 mg of 5-vinyl-araU. 0.36 ml of a dimethylformamide solution containing 53 mg of chlorine was then further added. The mixture was subjected to reaction at 90° to 100° C. for 4 hours. The reaction mixture was then cooled and concentrated under reduced pressure. The resulting residue was dissolved in methanol and then was charged onto 10 PTLC's, each being 20 cm×20 cm carrying 10 g silica gel on it, and developed Pharmacological Test 2

The effects of 5-bromovinyl araU and 5-chlorovinyl-araU on proliferation of HEL-F were compared with those of IDU and araA in accordance with the Machida et al. method (cf. Antimicrobial Agents and Chemotherapy, Vol. 16, No. 2, p. 158, 1979).

In the growth medium of HEL-F under proliferation (culture medium: Eagle's minimal essential medium supplemented with 10% fetal bovine serum) was added a test compound diluted in serial two-fold dilution and then incubated for 4 days. The numbers of increased cells with various concentrations of the compound tested were compared with those of the control groups wherein no compound was added. The concentration of the tested compounds which exhibited 50% inhibition of proliferation ($ID_{50}$) in comparison with the controls wherein no compound was added are shown in the following table.

| Compounds tested | $ID_{50}$ (μg/ml) |
| --- | --- |
| 5-bromovinyl-araU | >1000 |
| 5-chlorovinyl-araU | >500 |
| IDU | 6 |
| araA | 4 |

In comparison with conventional anti-virus agents IDU and araA, the 5-bromovinyl-araU and 5-chlorovinyl-araU have stronger anti-virus activities (Test 1), but exhibit markedly weak inhibition of cell proliferation (Test 2). Thus, 5-bromovinyl-araU and 5-chlorovinyl-araU are expected to be anti-virus agents which have lower toxicity than IDU and also have excellent efficacy on herpes virus-infected diseases and the like.

Pharmacological Test 3

In conformance with Pharmacological Tests 1 and 2, the anti-virus activities and cell proliferations of 5-bromovinyl-araU and 5-chlorovinyl-araU were compared with those of 5-vinyl-araU and 5-bromovinyl-2′-deoxyuridine (5-bromovinyl-dUrd). The results obtained were as follows.

| | Anti-HSV-1 | | Anti-HSV-2 | | Anti-VZV | | Anti-HEL-F |
| --- | --- | --- | --- | --- | --- | --- | --- |
| | MIC (μg/ml) | VR | MIC (μg/ml) | VR | MIC (μg/ml) | VR | $ID_{50}$ (μg/ml) |
| 5-Bromo-vinyl-araU | 0.032 | 3.7 | 100 | 0.9 | 0.1 | 3.5 | >1000 |
| 5-Chloro-vinyl-araU | 0.1 | 3.5 | >1000 | 0.2 | 0.1 | 3.4 | 1000 |
| 5-Vinyl-araU | 0.1 | 3.3 | 1 | 2.7 | 0.32 | 2.9 | 650 |
| 5-Bromo-vinyl-dUrd | 0.032 | 3.7 | 100 | 0.7 | — | — | 150 |

5-bromovinyl-araU and 5-chlorovinyl-araU have anti-virus activities of potencies similar to that of 5-bromovinyl-dUrd and have HEL-F proliferation inhibitory effects which are less than that of 5-bromovinyl-dUrd. Furthermore, in the comparison with 5-vinyl-araU, 5-bromovinyl-araU and 5-chlorovinyl-araU have a significantly greater anti-HSV-1 activity and a cell proliferation inhibiting activity of one half relative to 5-vinyl-araU. In addition, 5-halogenovinyl-araU is superior to 5-vinyl-araU in chemical stability against acids, alkalis, etc., and in physical stability against heat and other physical factors and has the advantageous feature of facility of synthesis and purification of compounds, preparation as a medicine, and preservation.

We claim:

1. An (E)-5-(2-halogenovinyl)-arabinofuranosyluracil represented by the formula [I],

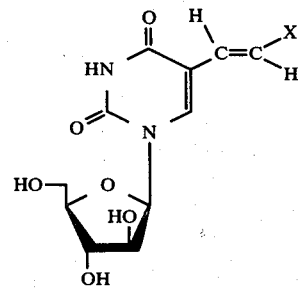

wherein X stands for a halogen.

2. The compound according to claim 1, in which the halogen is selected from the group consisting of chlorine, bromine and iodine.

3. The compound according to claim 2, in which the halogen is chlorine.

4. The compound according to claim 2, in which the halogen is bromine.

5. An anti-DNA virus agent comprising as the effective component an effective quantity of a compound represented by the formula [I],

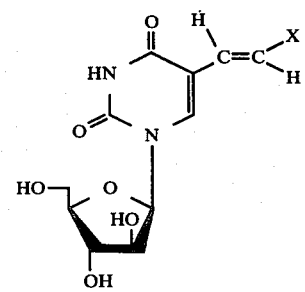

wherein X stands for a halogen and a pharmaceutically acceptable carrier.

6. The anti-DNA virus agent according to claim 5 in which the halogen is selected from the group consisting of chlorine, bromine and iodine.

* * * * *